US009084902B2

(12) United States Patent
Mordas et al.

(10) Patent No.: US 9,084,902 B2
(45) Date of Patent: Jul. 21, 2015

(54) NON-ALCHOHOL BIOACTIVE ESSENTIAL OIL MOUTH RINSES

(75) Inventors: Carolyn J. Mordas, Ewing, NJ (US); Robert J. Gambogi, Hillsborough, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 12/827,927

(22) Filed: Jun. 30, 2010

(65) Prior Publication Data

US 2012/0003163 A1 Jan. 5, 2012

(51) Int. Cl.
| | |
|---|---|
| *A61K 8/365* | (2006.01) |
| *A61Q 11/00* | (2006.01) |
| *A61K 8/02* | (2006.01) |
| *A61K 8/06* | (2006.01) |
| *A61K 8/34* | (2006.01) |
| *A61K 8/46* | (2006.01) |
| *A61K 8/92* | (2006.01) |
| *A61Q 17/00* | (2006.01) |

(52) U.S. Cl.
CPC .............. *A61Q 11/00* (2013.01); *A61K 8/0291* (2013.01); *A61K 8/068* (2013.01); *A61K 8/345* (2013.01); *A61K 8/463* (2013.01); *A61K 8/466* (2013.01); *A61K 8/922* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 3,959,458 A | 5/1976 | Agricola | |
| 4,051,234 A | 9/1977 | Gieske | |
| 4,150,151 A | 4/1979 | Pader et al. | |
| 4,411,813 A | 10/1983 | Voisin | |
| 4,894,220 A | 1/1990 | Nabi et al. | |
| 4,945,087 A * | 7/1990 | Talwar et al. | 514/60 |
| 5,190,747 A | 3/1993 | Sekiguchi | |
| 5,283,056 A | 2/1994 | Chung et al. | |
| 5,284,648 A | 2/1994 | White et al. | |
| 5,290,541 A | 3/1994 | Liang | |
| 5,292,527 A | 3/1994 | Konopa | |
| 5,320,863 A | 6/1994 | Chung et al. | |
| 5,407,662 A | 4/1995 | Mackles et al. | |
| 5,466,437 A * | 11/1995 | Gaffar et al. | 424/52 |
| 5,681,548 A * | 10/1997 | Esposito et al. | 424/49 |
| 5,707,610 A | 1/1998 | Ibsen et al. | |
| 5,723,106 A | 3/1998 | Buch et al. | |
| 5,733,530 A | 3/1998 | Bacca et al. | |
| 5,817,295 A | 10/1998 | Chaudhari et al. | |
| 5,891,422 A | 4/1999 | Pan et al. | |
| 5,945,087 A | 8/1999 | Nelson et al. | |
| 6,045,813 A | 4/2000 | Ferguson | |
| 6,106,815 A | 8/2000 | Kang | |
| 6,121,315 A | 9/2000 | Nair | |
| 6,136,298 A | 10/2000 | Gaffar et al. | |
| 6,261,540 B1 | 7/2001 | Nelson | |
| 6,348,187 B1 | 2/2002 | Pan et al. | |
| 6,416,745 B1 | 7/2002 | Markowitz | |
| 6,585,961 B1 | 7/2003 | Stockel | |
| 6,682,722 B2 | 1/2004 | Majeti et al. | |
| 6,797,683 B2 | 9/2004 | Shana'a | |
| 7,084,104 B2 | 8/2006 | Martin | |
| 7,087,650 B2 | 8/2006 | Lennon | |
| 2004/0047822 A1 | 3/2004 | Zamudo Tena | |
| 2005/0014827 A1 | 1/2005 | Schur | |
| 2006/0013778 A1 | 1/2006 | Hodosh | |
| 2006/0105000 A1 | 5/2006 | Friedman | |
| 2008/0038210 A1 | 2/2008 | Yano et al. | |
| 2008/0085246 A1 | 4/2008 | Rabenhorst et al. | |
| 2008/0171089 A1 | 7/2008 | Blondino et al. | |
| 2008/0219935 A1 | 9/2008 | Kwak et al. | |
| 2008/0247966 A1 | 10/2008 | Natsch et al. | |
| 2008/0247972 A1 | 10/2008 | Conceicao | |
| 2011/0070306 A1 * | 3/2011 | Baker et al. | 424/484 |

FOREIGN PATENT DOCUMENTS

| | | |
|---|---|---|
| CN | 1086994 A | 5/1994 |
| CN | 1662213 A | 5/2002 |
| EP | 0338978 A2 | 10/1989 |
| JP | 2009096724 A | 5/2009 |
| WO | WO 94/23691 A2 | 10/1994 |
| WO | WO9616633 | 6/1996 |
| WO | WO 97/30685 * | 8/1997 |
| WO | WO9730685 | 8/1997 |
| WO | WO9840094 | 9/1998 |
| WO | WO 2005/123028 A1 | 12/2005 |
| WO | WO2008016837 | 2/2008 |
| WO | WO 2008/069631 A1 | 6/2008 |
| WO | WO2009019604 | 2/2009 |

OTHER PUBLICATIONS

European Search Report for EPA No. 11172281.5 dated Apr. 24, 2013.

* cited by examiner

*Primary Examiner* — Snigdha Maewall

(57) ABSTRACT

The invention relates generally to mouth rinses for the prevention and elimination of bad breath as well as for the reduction of oral microorganisms responsible for the development of dental plaque and tooth decay. In particular, the present invention relates to a non-alcohol or reduced alcohol mouth rinses effective at preventing the above-mentioned problems.

20 Claims, No Drawings

NON-ALCHOHOL BIOACTIVE ESSENTIAL OIL MOUTH RINSES

FIELD OF THE INVENTION

The invention relates generally to mouth rinses for the prevention and elimination of bad breath as well as for the reduction of oral microorganisms responsible for the development of dental plaque and tooth decay. In particular, the present invention relates to a non-alcohol or reduced alcohol mouth rinses effective at preventing the above-mentioned problems.

BACKGROUND OF THE INVENTION

Mouth rinse or mouthwash compositions have been used by people for many years for the prevention of bad breath and for the elimination of bacteria and other oral microorganisms that are responsible not only for bad breath but also tooth decay, plaque and gum diseases such as gingivitis and periodontitis. To this end, antiseptic mouthwashes in the past have been designed to clean the oral cavity, provide fresh breath and kill these pathogenic microbes.

Leading antiseptic mouth rinses have traditionally contained alcohol (i.e., ethanol) at fairly high levels, ranging from approximately 20% up to about 30% by volume, based on the total mouthwash volume (hereinafter referred to as "% v/v"). Alcohol is used both as a vehicle and as a solvent in which the active ingredients, and additives such as astringents, fluorides, color additives, flavor oils, and the like, can be dissolved and then dispersed into solution. Alcohol also provides a preservative role for the mouth rinse during storage and use, and enhances the flavor oil organoleptic cues.

However, the use of high levels of alcohol may sometimes be found unacceptable by some mouthwash users. Senior citizens have also complained about problems related to gargling with such mouth rinses, and chronic exposure has been found to result in a feeling of gum "burn" resulting from the high concentrations of alcohol. It has also been reported that alcoholic mouth rinses can result in an unpleasant "dry mouth" sensation.

On the other hand, reducing the levels of alcohol in these mouth rinse compositions can have significant disadvantages. It has been found that lower alcohol concentrations result not only in a loss in the solubility of the actives and other ingredients in the composition, but also in a noticeable decrease in the ability of the composition to kill the oral microorganisms responsible for bad breath, plaque and gum disease. This loss in antimicrobial activity is not only due to the reduction of alcohol as a vehicle, but also to the reduced bioavailability of the solubilized actives.

Thymol, for example, is a well known antiseptic compound, also known as an essential oil, which is utilized for its antimicrobial activity in a variety of mouthwash or mouth rinse preparations. In particular, thymol can be utilized in oral hygiene compositions such as mouth rinses in sufficient quantities to provide desired beneficial therapeutic effects. Mouthwashes with thymol are well-known, and have been used by millions of people for over one hundred years. They have been proven effective in killing microbes in the oral cavity that are responsible for plaque, gingivitis and bad breath. Thymol, together with other essential oils such as methyl salicylate, menthol and eucalyptol, comprise the active component in some antiseptic mouth rinses. These oils achieve good efficacy although present in small amounts. Without being restricted to any specific theory, it is now believed that the efficacy and taste of antiseptic mouth rinses may be due to the improved dispersion or dissolution of the oils and bioavailability after such dispersion or dissolution of these four active ingredients.

The above described dispersion or dissolution is also important from an aesthetic point of view since a clear mouth rinse solutions are certainly more preferred by consumers than cloudy, turbid or otherwise heterogeneous ones. Obviously then, there is a substantial need for the development of a reduced and/or no alcohol mouth rinses which provide improved dispersion or dissolution of the essential oils yet maintain the bioavailability of the essential oils for preventing bad breath, killing oral microbes and reducing or eliminating plaque.

SUMMARY OF THE INVENTION

In certain embodiments, the present invention is a reduced alcohol or non-alcohol, antimicrobial mouth rinse composition, comprising: (a) an oil phase comprising at least one antimicrobial essential oil; (b) a solvent system comprising a polyol solvent and a sugar alcohol solvent; (c) an alkylsulfate surfactant; and (d) water.

In further embodiments, the reduced alcohol or non-alcohol, antimicrobial mouth rinse composition is a microemulsion comprising micelles having an aggregate size of less than about 200 nm.

In still further embodiments, the reduced alcohol or non-alcohol, antimicrobial mouth rinse composition of the present invention exhibits a high level of antimicrobial activity as measured by an M-factor greater than 0.5 (or about 0.5), optionally 1.0 (or about 1.0) optionally, 2.0 (or about 2.0), or optionally 3.0 (or about 3.0) where "M-factor" equals the log RLU value of water used as the negative control minus the log RLU value of the mouth rinse composition being tested. In addition, the oral mouth rinse compositions of this invention are clear (to the unaided human eye) and aesthetically appealing products.

In further embodiments, the reduced alcohol or non-alcohol, antimicrobial mouth rinse composition of the present invention comprises (a) an antimicrobially effective amount of one or more antimicrobial essential oils; (b) a co-solvent of a glycol and a polyol; (c) an alkylsulfate surfactant; and (d) water.

DETAILED DESCRIPTION OF THE INVENTION

The compositions of the present invention can comprise, consist of, or consist essentially of the essential elements and limitations of the invention described herein, as well any of the additional or optional ingredients, components, or limitations described herein. The term "comprising" (and its grammatical variations) as used herein is used in the inclusive sense of "having" or "including" and not in the exclusive sense of "consisting only of."

The terms "a" and "the" as used herein are understood to encompass the plural as well as the singular.

Unless otherwise indicated, all documents cited are, in relevant part, incorporated herein by reference; the citation of any document is not to be construed as an admission that it is prior art with response to the present invention. Furthermore, all documents incorporated herein by reference in their entirety are only incorporated herein to the extent that they are not inconsistent with this specification.

The reduced alcohol or non-alcohol mouthwash and mouth rinse compositions described herein provide an antimicrobially effective amount of one or more antimicrobial essential oils towards oral microorganisms responsible for oral malodor and the build-up of plaque and calculus and the resulting tooth and gum diseases that may follow.

The phrase "antimicrobially effective amount" means the concentration or quantity or level of the compound of the present invention that can attain a particular medical end in having toxic activity for oral microorganisms.

The phrase "orally acceptable" means that the carrier is suitable for application to the surfaces of the oral cavity or ingestion by a living organism including, but not limited to, mammals and humans without undue toxicity, incompatibility, instability, allergic response, and the like.

All percentages, parts and ratios are based upon the total weight of the composition of the present invention, unless otherwise specified. All such weights as they pertain to the listed ingredients are based on the level of the particular ingredient described and, therefore, do not include carriers or by-products that may be included in commercially available materials, unless otherwise specified.

The phrase "reduced level" of alcohol means an amount of a $C_2$-$C_4$ monohydric alcohol up to 10% v/v (or about 10% v/v), optionally, up to 5% v/v (or about 5% v/v), optionally, up to 1.0% v/v (or about 1.0% v/v), optionally up to 0.1% v/v (or about 0.1% v/v) by volume of the total composition. Optionally, the compositions of the present invention are free of $C_2$-$C_4$ monohydric alcohols.

The term "sterile water", as used herein, means sterile water for irrigation/injection U.S.P. The USP designation means that the sterile water for irrigation/injection is the subject of an official monograph in the current (as of the filing date of this application) US Pharmacopeia.

Unless otherwise specified, the term "oil(s)" or "oily" component means any hydrophobic, water immiscible component, including but not limited to, essential oils (such as menthol, thymol, eucalyptol and methyl salicylate), flavor oils and hydrophobic compounds such as vitamin E, vitamin E acetate, apigenin and triclosan and mixtures of any of the above hydrophobic, water immiscible components.

Oil Phase

The compositions of the present invention comprise an oil phase comprising at least one oil. In certain embodiments the oil phase of the present invention comprises at least one antimicrobial essential oil.

Antimicrobial Essential Oils

In certain embodiments, the enhanced antimicrobial efficacy of the non-alcohol mouth rinse compositions herein is attributed to the presence of minor amounts of one or more antimicrobial or bioactive essential oils (i.e. thymol, eucalyptol, menthol and methyl salicylate).

Thymol, [$(CH_3)_2CHC_6H_3(CH_3)OH$, also known as isopropyl-m-cresol], is only slightly soluble in water but is soluble in alcohol, and its presence is one of the reasons alcohol was necessary in the well-established, high alcohol commercial mouth rinses. Methyl salicylate, [$C_6H_4OHCOOCH_3$, also known as wintergreen oil], additionally provides flavoring to the together with its antimicrobial function. Eucalyptol ($C_{10}H_{18}O$, also known as cineol) is a terpene ether and provides a cooling, spicy taste. Eucalyptol may be used in place of thymol in certain formulations in the same amount if desired. Menthol ($CH_3C_6H_9(C_3H_7)OH$), also known as hexahydrothymol) is also only slightly soluble in alcohol, and is fairly volatile. Menthol, in addition to any antiseptic properties, provides a cooling, tingling sensation.

In certain embodiments, the essential oils are used in amounts effective to provide antimicrobial activity in the oral cavity. In specific embodiments, the total amount of essential oils present in the disclosed compositions can be from 0.001% (or about 0.001%) to 0.35% (or about 0.35%) w/v, or optionally from 0.16% (or about 0.16%) to 0.28% (or about 0.28%) w/v of the composition.

In some embodiments, the compositions of the present invention contain thymol and additionally eucalyptol, menthol, or methyl salicylate, or mixtures thereof. Optionally, the composition contains all four of these essential oils.

In certain embodiments, thymol is employed in amounts of from 0.001% (or about 0.001%) to 0.25% (or about 0.25%) w/v, or optionally from 0.04% (or about 0.04%) to 0.07% (or about 0.07%) w/v of the composition. In certain embodiments, eucalyptol may be employed in amounts of from 0.001% (or about 0.001%) to 0.11% (or about 0.11%) w/v, or optionally from 0.085% (or about 0.085%) to 0.10% (or about 0.10%) w/v of the composition. In certain embodiments, menthol is employed in amounts of from 0.001% (or about 0.001%) to 0.25% (or about 0.25%) w/v, or optionally from 0.035% (or about 0.035%) to 0.05% (or about 0.05%) w/v of the composition. In certain embodiments, methyl salicylate is employed in amounts of from 0.001% (or about 0.001%) to 0.08% (or about 0.08%) w/v, or optionally from 0.04% (or about 0.04%) to 0.07% (or about 0.07%) w/v of the composition.

In some embodiments, the carrier for the essential oils (the active ingredients) is typically a water-alcohol mixture, generally water-ethanol. In the past, some antiseptic oral mouth rinse compositions, required ethanol levels of up to about 27% v/v. These high levels were necessary to assist the actives in providing the necessary antimicrobial functionality as well as providing a clear, aesthetically attractive liquid medium. Merely reducing the alcohol levels, without the addition of other formulation components, results in a cloudy, less efficacious product.

Without being bound to any theory, it is believed that in these high alcohol level oral compositions, the alcohol solubilizes the antimicrobial essential oils and in so doing acts by an active enhancement mechanism. The antimicrobial essential oils are more readily dispersed throughout the solution and remain free or unbound to attack pathogenic microbes throughout the oral cavity. Reducing the alcohol levels was believed to adversely affect this enhancement mechanism. In accordance with the present invention, however, it was surprisingly and unexpectedly found that the level of alcohol can be reduced or eliminated without sacrificing antimicrobial efficacy or clarity if the mouth rinse composition contains a solvent system and alkyl sulfate surfactant as taught herein.

In certain embodiments, the total amount of oil phase present in the disclosed compositions of the present invention should not exceed 1.35% w/v (or about 1.35% w/v) of the mouth rinse composition. Optionally, the total oil phase, can be present in an amount of from 0.04% (or about 0.04%) to 1.35% (or about 1.35%) w/v, or optionally from 0.10% (or about 0.10%) to 0.4% (or about 0.4%) w/v of the mouth rinse composition.

Solvent System

In certain embodiments, the mouth rinse compositions of the present invention also include a solvent system comprising at least one polyol solvent and at least one sugar alcohol.

Polyol Solvent

Polyol or polyhydric alcohol solvents suitable for use in the solvent system of the present invention includes polyhydric alkanes (such as propylene glycol, glycerin, butylene glycol, hexylene glycol, 1,3-propanediol); polyhydric alkane esters (dipropylene glycol, ethoxydiglycol); polyalkene glycols (such as polyethylene glycol, polypropylene glycol) and mixtures thereof. In certain embodiments, the polyol solvent can be present in an amount of from 1.0% (or about 1.0%) to 30.0% (or about 30.0%) w/v, or optionally from 5.0% (or about 5.0%) to 15.0% (or about 15.0%) w/v of the composition.

Sugar Alcohol Solvent

The sugar alcohol solvent(s) may be selected from those multi-hydroxy-functional compounds that are conventionally used in oral and ingestible products. In certain embodiments, the sugar alcohol (s) should be non-metabolized and non-fermentable sugar alcohol (s). In specific embodiments, the sugar alcohols include, but are not limited to xylitol, sorbitol, mannitol, maltitol, inositol, allitol, altritol, dulcitol, galactitol, glucitol, hexitol, iditol, pentitol, ribitol, erythritol and mixtures thereof. Optionally, the sugar alcohol is selected from the group consisting of sorbitol and xylitol or mixtures thereof. Optionally, the sugar alcohol is sorbitol.

In certain embodiments, the total amount of sugar alcohol (s) which are added to effectively aid in the dispersion or dissolution of the active ingredients should not exceed 17% w/v (or about 17% w/v) of the composition. Optionally, total amount of sugar alcohol should not exceed 10% w/v (or about 10% w/v) of the composition. The sugar alcohol can be in an amount of from 1.0% (or about 1.0%) to 17.0% (or about 17.0%) w/v, or optionally from 5.0% (or about 5.0%) to 15.0% (or about 15.0%) w/v of the composition.

In certain embodiments, the total amount of the solvent system which is added to effectively aid in the dissolution or dispersion of the active ingredients should not exceed 47% w/v (or about 47% w/v) of the composition. Optionally, total amount of solvent system should not exceed 20% w/v (or about 20% w/v) of the composition. The solvent system can be in an amount of from 2% (or about 2%) to 47% (or about 47%) w/v, or optionally from 10% (or about 10%) to 20% (or about 20%) w/v of the composition.

In certain embodiments, the ratio of the sugar alcohol to the polyol solvent in the composition should be from 10:1 (or about 10:10) to 1:10 (or about 1:10), optionally from 5:1 (or about 5:1) to 1:5 (or about 1:5), optionally 1:1 (or about 1:1) by weight.

Alkyl Sulfate Surfactant

The mouth rinse compositions of the present invention also contain at least one alkyl sulfate surfactant. In certain embodiments, suitable alkyl sulfate surfactants include, but are not limited to sulfated $C_8$ to $C_{18}$, optionally sulfated $C_{10}$ to $C_{16}$ even numbered carbon chain length alcohols neutralized with a suitable basic salt such as sodium carbonate or sodium hydroxide and mixtures thereof such that the alkyl sulfate surfactant has an even numbered $C_8$ to $C_{18}$, optionally $C_{10}$ to $C_{16}$, chain length. In certain embodiments, the alkyl sulfate is selected from the group consisting of sodium lauryl sulfate, hexadecyl sulfate and mixtures thereof. In certain embodiments, commercially available mixtures of alkyl sulfates are used. A typical percentage breakdown of alkyl sulfates by alkyl chain length in commercially available sodium lauryl sulfate (SLS) is as follows:

| Alkyl Chain Length | Component Percentage in SLS |
| --- | --- |
| $C_{12}$ | >60% |
| $C_{14}$ | 20%-35% |
| $C_{16}$ | <10% |
| $C_{10}$ | <1% |
| $C_{18}$ | <1% |

Suitable commercially available mixtures include Stepanol WA-100 NF USP, (Stepan, Northfield, Ill.), Texapon K12 G PH, (Texapon, Cognis, Germany) and mixtures thereof.

In certain embodiments, where the amount of the alkyl sulfate surfactant added to the composition can be from 0.05% (or about 0.05%) to 2.0% (or about 2.0%) w/v, or optionally from 0.1% (or about 0.1%) to 0.5% (or about 0.5%) w/v of the composition.

Additional surfactants may be added with the alkyl sulfate surfactant to aid in solubilization of the essential oils provided such surfactants do not affect the bioavailability of the essential oils. Suitable examples include additional anionic surfactants, nonionic surfactants, amphoteric surfactants and mixtures thereof. However, in certain embodiments, the total surfactant concentration (including the alkyl sulfate surfactant alone or in combination with other surfactants) of the mouth rinses of the present invention should not exceed or should be less than 2% (or about 2%), optionally, the total surfactant concentration should not exceed or should be less than 1.5% (or about 1.5%), optionally, the total surfactant concentration should not exceed or should be less than 1.0% (or about 1.0%), optionally, the total surfactant concentration should not exceed or should be less than 0.5% (or about 0.5%) by weight of the composition.

Anionic surfactants useful herein include, but are not limited to, sarcosine type surfactants or sarcosinates; taurates such as sodium methyl cocoyl taurate; sodium lauryl sulfoacetate; sodium lauroyl isethionate; sodium laureth carboxylate; sodium dodecyl benzenesulfonate and mixtures thereof. Many suitable anionic surfactants are disclosed in U.S. Pat. No. 3,959,458, to Agricola, et al., herein incorporated by reference in its entirety.

Nonionic surfactants which can be used in the compositions of the present invention include, but are not limited to, compounds produced by the condensation of alkylene oxide groups (hydrophilic in nature) with an organic hydrophobic compound which may be aliphatic or alkyl-aromatic in nature. Examples of suitable nonionic surfactants include, but are not limited to, alkyl polyglucosides; ethoxylated hydrogenated castor oils available commercially for example under the trade name CRODURET (Croda Inc., Edison, N.J.), and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof.

The amphoteric surfactants useful in the present invention include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium lauroamphoacetate and mixtures thereof. Mixtures of any of the above mentioned surfactants can also be employed. A more detailed discussion of anionic, nonionic and amphoteric surfactants can be found in U.S. Pat. No. 7,087,650 to Lennon; U.S. Pat. No. 7,084,104 to Martin et al.; U.S. Pat. No. 5,190,747 to Sekiguchi et al.; and U.S. Pat. No. 4,051,234, Gieske, et al., each of which patents are herein incorporated by reference in their entirety.

In certain embodiments, the additional surfactant to be added the mouth rinses of the present invention with the alkyl sulfate surfactant is selected from the group consisting of taurates. Optionally, the additional surfactant is selected from the group consisting of sodium methyl lauryl taurate, sodium methyl oleoyl taurate, sodium methyl cocoyl taurate and mixtures thereof. In certain embodiments, the additional surfactant is sodium methyl cocoyl taurate.

In certain embodiments, the ratio of the solvent system to the total amount of surfactant in the composition should be from 360:1 (or about 360:1) to 10:1 (or about 10:1), optionally from 100:1 (or about 100:1) to 20:1 (or about 20:1) by weight.

In further embodiments, the ratio of the oil phase to the solvent system to the total amount of surfactant (or, the total surfactant concentration including the alkyl sulfate surfactant) by weight is 1:200:1.5 (or about 1:200:1.5) or, optionally, 1:60:1.5 (or about 1:60:1.5) by weight.

Aqueous Phase

An aqueous phase comprising water is added to the oil phase of the present compositions to form oil-in-water or water-in-oil dispersions, micro emulsions or emulsions.

In certain embodiments, the aqueous phase comprises from about 60% to about 95%, or optionally from about 75% to about 93%, by weight of the composition.

Alternatively, the mouth rinse compositions of the present invention may be formulated in a dry powder, chewing gum, semi-solid, solid or liquid concentrate form. In such embodiments, for example, water is added to q.s. as necessary in the case of liquid concentrates or powdered formulations, or water may be removed using standard evaporation procedures known in the art to produce a composition in dry powder form. Evaporated, or freeze dried forms are advantageous for storage and shipping.

Micelle Size

The mouth rinse compositions of the present invention comprise colloidal aggregates of amphipathic molecules called micelles. In certain embodiments, the micelles of the present invention have an aggregate size of less than 200 nm (or about 200 nm), optionally 100 nm (or about 100 nm), optionally 50 nm (or about 50 nm), or optionally 10 nm (or about 10).

Optional Ingredients

Insoluble Particulates

In certain embodiments, the oral care compositions of the present invention optionally comprise a safe and effective amount of a water insoluble particulate. The water insoluble particulate can be an abrasive particle (such as a dentally acceptable abrasive) or non-abrasive particulate.

In certain embodiments, dentally acceptable abrasives include, but are not limited to, water insoluble calcium salts such as calcium carbonate, and various calcium phosphates, alumina, silica, synthetic resins and mixtures thereof. Suitable dentally acceptable abrasives may generally be defined as those having a radioactive dentine abrasion value (RDA) of from about 30 to about 250 at the concentrations used in the compositions of the present invention. In certain embodiments, abrasives are non-crystalline, hydrated, silica abrasives, particularly in the form of precipitated silica or milled silica gels available commercially, for example, under the trade names ZEODENT (J. M. Huber Corporation, Edison, N.J.), and SYLODENT (W.R. Grace & Co., New York, N.Y.), respectively. In certain embodiments, the compositions according to the present invention comprise from about 1% to about 20%, or, optionally, from about 5% to about 10% by weight of the abrasive.

Alternatively, the insoluble particulate is a non-abrasive particulate which is visible to the unaided eye and stable in the compositions of the present invention.

The non-abrasive particulate can be of any size, shape, or color, according to the desired characteristic of the product. The non-abrasive particulates will typically have the shape of a small round or substantially round ball or sphere, however, platelet or rod-shaped configurations are also contemplated herein. Generally, a non-abrasive particulate has an average diameter of from about 50 µm to about 5000 µm, optionally from about 100 µm to about 3000 µm, or optionally from about 300 µm to about 1000 µm. By the terms "stable" and/or "stability", it is meant that the abrasive or non-abrasive particulates are not disintegrated, agglomerated, or separated under normal shelf conditions. In certain embodiments, the terms "stable" and/or "stability" further mean that the compositions of present invention contain no visible or minimally visible (to the unaided eye) signs of sedimentation of the insoluble particulates after 8 weeks, optionally 26 weeks, optionally 52 weeks, at room temperature.

The non-abrasive particulates herein are typically incorporated in the present compositions at levels of from about 0.01% to about 25%, optionally, from about 0.01% to about 5%, or optionally from about 0.05% to about 3%, by weight of the composition.

The non-abrasive particulate herein will typically comprise a structural material and/or, optionally, an encompassed material.

The structural material provides a certain strength to the non-abrasive particulates so that they retain their distinctively detectable structure in the compositions of the present invention under normal shelf conditions. In one embodiment, the structural material further can be broken and disintegrated with very little shear on the teeth, tongue or oral mucosa upon use.

The non-abrasive particulates can be solid or liquid, filled or un-filled, as long as they are stable in the compositions of the present invention. The structural material used for making the non-abrasive particulates varies depending on the compatibility with other components, as well as material, if any, to be encompassed in the non-abrasive particulates. Exemplary materials for making the non-abrasive particulates herein include: polysaccharide and saccharide derivatives such as crystalline cellulose, cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, gum acacia (gum arabic), agar, agarose, maltodextrin, sodium alginate, calcium alginate, dextran, starch, galactose, glucosamine, cyclodextrin, chitin, amylose, amylopectin, glycogen, laminaran, lichenan, curdlan, inulin, levan, pectin, mannan, xylan, alginic acid, arabic acid, glucommannan, agarose, agaropectin, prophyran, carrageenen, fucoidan, glycosaminoglycan, hyaluronic acid, chondroitin, peptidoglycan, lipopolysaccharide, guar gum, starch, and starch derivatives; oligosaccharides such as sucrose, lactose, maltose, uronic acid, muramic acid, cellobiose, isomaltose, planteose, melezitose, gentianose, maltotriose, stachyose, glucoside and polyglucoside; monosaccharides such as glucose, fructose, and mannose; synthetic polymers such as acrylic polymers and copolymers including polyacrylamide, poly(alkyl cyanoacrylate), and poly(ethylene-vinyl acetate), and carboxyvinyl polymer, polyamide, poly(methyl vinyl ether-maleic anhydride), poly (adipyl-L-lysine), polycarbonate, polyterephthalamide, polyvinyl acetate phthalate, poly(terephthaloyl-L-lysine), polyarylsulfone, poly(methylmethacrylate), poly($\epsilon$-caprolactone), polyvinylpyrrolidone, polydimethylsiloxane, polyoxyethylene, polyester, polyglycolic acid, polylactic acid, polyglutamic acid, polylysine, polystyrene, poly(styreneacrylonitrile), polyimide, and poly(vinyl alcohol); and other material such as fat, fatty acid, fatty alcohol, milk solids, molasses, gelatin, gluten, albumin, shellac, caseinate, bees wax, carnauba wax, spermaceti wax, hydrogenated tallow, glycerol monopalmitate, glycerol dipalmitate, hydrogenated castor oil, glycerol monostearate, glycerol distearate, glycerol tristearate, 12-hydroxystearyl alcohol, protein, and protein derivatives; and mixtures thereof. Components herein may be described in other sections as useful components for the present composition. In certain embodiments, the components as described in this section form the structure of the non-abrasive particulates so as to not be substantially dissolved or dispersed from the particulates and into the compositions of the present invention under normal shelf conditions.

In other embodiments, the structural material herein comprises components selected from the group consisting of polysaccharides and their derivatives, saccharides and their derivatives, oligosaccharides, monosaccharides, and mixtures thereof, or optionally, comprises components are having various degrees of water solubility. In some embodiments, the structural material comprises lactose, cellulose, and hydroxypropyl methylcellulose.

Suitable non-abrasive particulates also include organogel particles as described in detail in U.S. Pat. No. 6,797,683, herein corporate by reference in its entirety. Non-abrasive particulates that are organogel particles typically comprise a structural material selected from waxes (e.g., beeswax, paraffin, water-insoluble wax, carbon-based wax, silicone wax, microcrystalline wax, etc.), triglycerides, acid triglycerides, polymers, fluoroalkyl (meth)acrylate polymers and copolymers, acrylate polymers, ethylene/acrylate copolymers, polyethylene, polypropylene polymers and copolymers, fatty acids, fatty alcohols, fatty acid esters, fatty acid ethers, fatty acid amides, alkylene polyhydric alcohols, fatty acid amide of an alkanolamine, glyceryl monostearate, (aryl-substituted) sugars, dibenzyl sorbitol (or mannitoal, rabbitol, etc.), condensates and precondensates of lower monohydric alcohols, trihydroic alcohols, lower polyglycols, propylene/ethylene polycondensates, and the like. Optionally, structural material for non-abrasive particulates that are organogel particles include beeswax, carnauba wax, low molecular weight ethylene homopolymers (e.g. Polywax 500, Polywax 1000, or Polywax 2000 polyethylene materials available from Baker Petrolite Corp.), or paraffin wax.

The non-abrasive particulates herein may encompass, contain, or be filled with an encompassed material. Such encompassed material can be water soluble or water insoluble. Suitable encompassed materials include benefit agents as described herein such as: oral care actives, vitamins, pigments, dyes, antimicrobial agents, chelating agents, optical brighteners, flavors, perfumes, humectants, minerals, and mixtures thereof. The encompassed materials herein are substantially retained within the non-abrasive particulates, and are substantially not dissolved from the particulates and into the compositions of the present composition under normal shelf conditions.

Particularly useful commercially available non-abrasive particulates herein are those with tradenames Unisphere and Unicerin available from Induchem AG (Switzerland), and Confetti Dermal Essentials available from United-Guardian Inc. (NY, USA). Unisphere and Unicerin particles are made of microcrystalline cellulose, hydroxypropyl cellulose, lactose, vitamins, pigments, and proteins. Upon use, the Unisphere and Unicerin particles can be disintegrated with very little shear and with practically no resistance, and readily disperse in the compositions of the present invention.

Suitable non-abrasive particulates for incorporation in the present compositions are described in detail in U.S. Pat. No. 6,797,683 (organogel particles); U.S. Pat. No. 6,045,813 (rupturable beads); U.S. Pat. Publ. 2004/0047822 A1 (visible capsules); and U.S. Pat. No. 6,106,815 (capsulated or particulated oily substances), each of which patent documents are herein incorporated by reference in their entirety.

In certain embodiments, the abrasive and/or nonabrasive particles have a density different or, optionally, substantially different from the carrier in which these particles are formulated.

Flavors or Flavorants

In certain embodiments, flavors or flavorants may also be added to further modify or magnify the taste of the mouth rinse, or reduce or mask the sharp "bite" or "burn" of ingredients such as thymol. Suitable flavors include, but are not limited to, oil of anise, anethole, benzyl alcohol, spearmint oil, citrus oils, vanillin and the like may be incorporated. In these embodiments, the amount of flavor oil added to the composition can be from 0.001% (or about 0.001%) to 1.0% (or about 1.0%) w/v, or optionally from 0.1% (or about 0.10%) to 0.30% (or about 0.30%) w/v of the composition.

The particular flavors or flavorants, and other taste-improving ingredients, employed will vary depending upon the particular taste and feel desired. Those skilled in the art can select and customize these types of ingredients to provide the desired results.

Buffers

In certain embodiments, additional conventional components may be added as in mouthwashes and mouth rinses of the prior art. Whereas some alcohol containing mouth rinses have a pH of about 7.0, reduction of the alcohol level may require the addition of acidic preservatives, such as sorbic acid or benzoic acid, which reduce pH levels. Buffer systems are then necessary to control the pH of the composition at optimal levels. This is generally accomplished through the addition of a weak acid and its salt or a weak base and its salt. In some embodiments, useful systems have been found to be sodium benzoate and benzoic acid in amounts of from 0.01% (or about 0.01% w/v) to 1.0% w/v (or about 1.0% w/v) of the composition, and sodium citrate and citric acid in amounts of from 0.001% (or about 0.001% w/v) to 1.0% w/v (or about 1.0% w/v) of the composition, phosphoric acid and sodium/potassium phosphate of amounts from 0.01% (or about 0.01%) to 1.0% (or about 1.0%) by weight of the composition. In certain embodiments, the buffers are incorporated in amounts that maintain the pH at levels of from 3.0 (or about 3.0) to 8.0 (or about 8.0), optionally from 3.5 (or about 3.5) to 6.5 (or about 6.5), optionally from 3.5 (or about 3.5) to 5.0 (or about 5.0). Without being limited by any theory, it is believed that these pH levels provide the essential oils with an environment that also maximizes their antimicrobial activity and promotes stability.

Fluoride Releasing Compounds

In certain embodiments, fluoride providing compounds may be present in the mouth rinse compositions of this invention. These compounds may be slightly water soluble or may be fully water soluble and are characterized by their ability to release fluoride ions or fluoride containing ions in water. Typical fluoride providing compounds are inorganic fluoride salts such as soluble alkali metal, alkaline earth metal, and heavy metal salts, for example, sodium fluoride, potassium fluoride, ammonium fluoride, cupric fluoride, zinc fluoride, stannic fluoride, stannous fluoride, barium fluoride, sodium hexafluorosilicate, ammonium hexafluorosilicate, sodium fluorozirconate, sodium monofluorophosphate, aluminum mono- and difluorophosphate and fluorinated sodium calcium pyrophosphate. Amine fluorides, such as N'-octadecyltrimethylendiamine-N,N,N'-tris(2-ethanol)-dihydrofluoride and 9-octadecenylamine-hydrofluoride), may also be used.

In certain embodiments, the fluoride providing compound is generally present in an amount sufficient to release up to 0.15% (or about 0.15%), optionally 0.001% (or about 0.001%) to 0.1% (or about 0.1%), optionally from 0.001% (or about 0.001%) to 0.05% (or about 0.05%) fluoride by weight of the composition.

Zinc Salts

In certain embodiments, zinc salts such as zinc chloride, zinc acetate or zinc citrate may be added as an astringent for an "antiseptic cleaning" feeling, as a breath protection enhancer or as anticalculus agent in an amount of from 0.0025% w/v (or about 0.0025% w/v) to 0.1% w/v (or about 0.1% w/v) of the composition.

Sensitivity Reducing Agents

In certain embodiments, sensitivity reducing agents, namely potassium salts of nitrate and oxalate in an amount from 0.1% (or about 0.1%) to 5.0% (or about 5.0%) w/v of the composition may be incorporated into the present invention. Other potassium releasing compounds are feasible (e.g. KCl). High concentrations of calcium phosphates may also provide some added sensitivity relief. These agents are believed to work by either forming an occlusive surface mineral deposit on the tooth surface or through providing potassium to the nerves within the teeth to depolarize the nerves. A more detailed discussion of suitable sensitivity reducing can be found in US 20060013778 to Hodosh and U.S. Pat. No. 6,416,745 to Markowitz et al., both of which are herein incorporated by reference in their entirety.

Anticalculus Agents

In certain embodiments, compounds with anti-calculus benefits (e.g. polyphosphates, phosphonates, various carboxylates, polyaspartic acid, inositol phosphate etc.) may be incorporated into the present invention. Also useful as an anticalculus agent are the anionic polymeric polycarboxylates. Such materials are well known in the art, being employed in the form of their free acids or partially or preferably fully neutralized water soluble alkali metal (e.g. potassium and preferably sodium) or ammonium salts. Preferred are 1:4 to 4:1 by weight copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and preferably S-97 Pharmaceutical Grade (M.W. 70,000), of GAF Chemicals Corporation.

Additional Ingredients

Although the mouth rinse compositions of the present invention may be formulated to be substantially clear and/or colorless to the unaided eye, acceptably approved food dyes are preferably used to provide a pleasing color to the compositions of the invention. These may be selected from, but not limited to, the long list of acceptable food dyes. Suitable dyes for this purpose include FD&C yellow #5, FD&C yellow #10, FD&C blue #1 and FD&C green #3. These are added in conventional amounts, typically in individual amounts of from 0.00001% w/v (or about 0.00001% w/v) to 0.0008% w/v (or about 0.0008% w/v), optionally from 0.00035% w/v (or about 0.00035% w/v) to 0.0005% w/v (or about 0.0005% w/v) of the composition.

Other conventional ingredients may be used in the mouth rinse compositions of this invention, including those known and used in the art. Examples of such ingredients include thickeners, suspending agents and softeners. Thickeners and suspending agents useful in the compositions of the present invention can be found in U.S. Pat. No. 5,328,682 to Pullen et al., herein incorporated by reference in its entirety. In certain embodiments, these are incorporated in amounts of from 0.1% w/v (about 0.1% w/v) to 0.6% w/v (or about 0.6% w/v), optionally 0.5% w/v (or about 0.5% w/v) of the composition.

A more detailed description of useful oral care actives and/or inactive ingredients and further examples thereof can be found in U.S. Pat. No. 6,682,722 to Majeti et al. and U.S. Pat. No. 6,121,315 to Nair et al., each of which are herein incorporated by reference in its entirety.

In certain embodiments, the compositions of the present invention are free of or essentially free of bioavailability affecting compounds. As used herein, "bioavailability affecting compound", means compounds that negatively affect the bioavailability of any incorporated essential oils such as by binding the essential oils or otherwise inactivating the essential oils. "Essentially free" as used with respect to bioavailability affecting compounds is defined as formulations having less than 5% (or about 5%), optionally, 3% (or about 3%), optionally, 1% (or about 1%), or optionally 0.1, or optionally, 0.01% (or about 0.01%), by weight (w/v) of the total composition of a bioavailability affecting compound. In certain embodiments, the bioavailability affecting compound can include, but is not limited to, polyethylene oxide/polypropylene oxide block copolymers such as poloxamers; cyclodextrins; polysorbates such as Tweens; and mixtures thereof.

Methods of Practicing the Present Invention

The invention illustratively disclosed herein may be practiced in the absence of any component, ingredient, or step which is not specifically disclosed herein.

In certain embodiments, the compositions of the present invention are applied to teeth and/or soft surfaces of the oral cavity for at least two consecutive applications, optionally, at least (or greater than) 3 (or about 3) or optionally, at least (or greater than) 5 (or about 5) consecutive applications.

When applied to teeth and/or soft surfaces of the oral cavity, in certain embodiments, the composition is allowed to remain in contact with the teeth and/or soft surfaces of the oral cavity for at least (or greater than) 10 (or about 10) seconds, optionally 20 (or about 20) seconds, optionally 30 (or about 30) seconds, optionally 50 (or about 50) seconds, or optionally 60 (or about 60) seconds.

Various embodiments of the invention have been set forth above. Each embodiment is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

EXAMPLES

The following examples are illustrative only and should not be construed as limiting the invention in any way. Those skilled in the art will appreciate that variations are possible which are within the spirit and scope of the appended claims.

Example 1

Solubilization of Essential Oils with Cyclodextrins

Comparative Example

Four formulations were prepared and tested for mixed-species biofilm kill analysis using a flow cell model. A 48-hour salivary biofilm was grown on a polystyrene peg plate (96 pegs, N=8 per test group). The pegs were subsequently treated for thirty seconds with each of the four formulations, as well as positive and negative controls. Treatments occurred twice daily for a total of five treatments. The positive control was a commercially available essential oil mouth rinse. The negative control was sterile water.

After treatment, viable bacteria remaining on the substrate were removed by sonication using a Misonix XL-2000 Ultrasonic processor (Qsonica, LLC, Newtown, Conn.). Using a Celsis Rapid Detection RapiScreen kit (Celsis International PLC, Chicago), the bacteria was lysed with Celsis Luminex and then the adenosine triphosphate (ATP) released from the lysed bacteria was measured using the bioluminescence marker Celsis LuminATE. Data was reported in log RLU (relative light units) where decreasing log RLUs indicates fewer viable bacteria remaining on the substrate and in M-factor units where M-factor is the difference between the log RLU values of the compound tested and the negative control.

The four formulations, as well as results of the mixed-species biofilm kill tests, are shown on Table 1. Final formulations were adjusted to pH 4.2 with 0.1M NaOH or 0.1M HCl if necessary.

The M-factors for formulations 1A through 1D were less than 0.1. This data indicates that the essential oils, though solubilized in the cyclodextrin formulas, are not sufficiently bio-available to kill bacterial species in a biofilm. The commercially available alcohol containing essential oil mouth rinse provided a relatively high M-factor with M-factor equal to 1.87.

Example 2

Various Surfactants

Seven propylene-glycol based mouth rinse formulations were prepared using various surfactants that are approved for use in oral care products and tested using an in-vitro single species S. mutans biofilm model. A 22-hour S. mutans biofilm was grown (N=32) and exposed to the formulations as well as positive and negative controls for 30 seconds. Sterile water was used as the negative control. After treatment the biofilm was neutralized and rinsed. The biofilm was harvested via sonication using a Misonix XL-2000 Ultrasonic processor (Qsonica, LLC, Newtown, Conn.). Using a Celsis Rapid Detection RapiScreen kit (Celsis International PLC, Chicago). The bacteria was lysed with Celsis Luminex and the ATP from the bacteria was measured using the bioluminescence marker Celsis LuminATE. Decreasing log RLUs (relative light units) indicates fewer bacteria alive after treatment.

The seven formulations, as well as results of the S. mutans biofilm kill tests, in log RLU and M-Factor units, are shown on Table 2. Final formulations were adjusted to pH 4.2 with 0.1M NaOH or 0.1M HCl if necessary. A typical M-factor for a commercially available alcohol containing essential oil mouth rinse is about 2.1 (log RLU of 5.8) in this model.

TABLE 1

| Ingredients | Formulations | | | | Positive Control (% w/w) | Negative Control (% w/w) |
|---|---|---|---|---|---|---|
| | 1A (% w/w) | 1B (% w/w) | 1C (% w/w) | 1D (% w/w) | | |
| Purified Water USP | QS | QS | QS | QS | QS | 100 |
| Hydroxypropyl Cyclodextrin | 2.00 | 2.00 | 0.00 | 2.00 | — | — |
| Poloxamer 407 | — | — | — | — | 0.25 | — |
| Thymol | 0.06 | 0.06 | — | — | 0.0636 | — |
| Menthol | 0.04 | 0.04 | — | — | 0.0420 | — |
| Eucalyptol | 0.09 | 0.09 | — | — | 0.0922 | — |
| Methyl Salicylate | 0.06 | 0.06 | — | — | 0.060 | — |
| Glycerin | 5.00 | 5.00 | 5.00 | 5.00 | — | — |
| Soribitol (70% solution) | 5.00 | 5.00 | 5.00 | 5.00 | 20.0 | — |
| Benzoic Acid | — | — | — | — | 0.12 | — |
| Citric Acid | 0.10 | 0.10 | 0.10 | 0.10 | — | — |
| NaOH | 0.25 | 0.25 | 0.25 | 0.25 | — | — |
| Ethanol-200 proof | — | 20.00 | 20.00 | — | 21.6 (v/v) | — |
| Flavor | — | — | — | — | 0.085 | — |
| Sweetener | — | — | — | — | 0.117 | — |
| Color | — | — | — | — | 0.0005 | — |
| Total | 100.00 | 100.00 | 100.00 | 100.00 | 100.00 | — |
| log RLU | 7.50 | 8.00 | 8.09 | 7.94 | 5.67 | 7.54 |
| M-factor | 0.04 | −0.46 | −0.55 | −0.40 | 1.87 | 0 |

TABLE 2

| Ingredients | 2A (% w/w) | 2B (% w/w) | 2C (% w/w) | 2D (% w/w) | 2E (% w/w) | 2F (% w/w) | 2G (% w/w) | Negative Control (% w/w) |
|---|---|---|---|---|---|---|---|---|
| Propylene glycol | 10.0 | 10.0 | 10.0 | 10.0 | 10.0 | 10.0 | 10.0 | 100 |
| Benzoic Acid | 0.30 | 0.30 | 0.30 | 0.30 | 0.30 | 0.30 | 0.30 | — |
| Menthol | 0.042 | 0.042 | 0.042 | 0.042 | 0.042 | 0.042 | 0.042 | — |
| Methyl salicylate | 0.060 | 0.060 | 0.060 | 0.060 | 0.060 | 0.060 | 0.060 | — |
| Thymol | 0.064 | 0.064 | 0.064 | 0.064 | 0.064 | 0.064 | 0.064 | — |
| Eucalyptol | 0.092 | 0.092 | 0.092 | 0.092 | 0.092 | 0.092 | 0.092 | — |
| Tween 20 | — | 2.00 | — | — | — | — | — | — |
| Sodium Lauryl Sulfate | 0.30 | — | 1.00 | — | — | 0.30 | 0.15 | — |
| Cocamidopropyl betaine | — | — | — | 1.00 | — | — | — | — |
| Hexadecyl sulfate | — | — | — | — | 0.30 | — | 0.15 | — |
| Sorbitol (70% solution) | — | — | — | — | — | 10.00 | — | — |
| Sodium Benzoate | 0.30 | 0.30 | 0.30 | 0.30 | 0.30 | 0.30 | 0.30 | — |
| Purified Water USP | QS | QS | QS | QS | QS | QS | QS | — |
| TOTAL | 100.0 | 100.0 | 100.0 | 100.0 | 100.0 | 100.0 | 100.0 | — |
| log RLU | 5.63 | 8.02 | 5.30 | 7.73 | 6.50 | 4.52 | 4.22 | 7.90 |
| M-factor | 2.27 | −0.12 | 2.60 | 0.17 | 1.40 | 3.38 | 3.68 | 0 |

Table 2 shows biocidal activity ranges significantly depending on the identity of the surfactant, with alkyl sulfates and alkyl sulfate combinations displaying the highest activity (M-factor greater than 2.0.) Additionally, it was observed that sorbitol increases bioactivity as well, as otherwise identical formulation 2A without sorbitol provided M-factor of 2.27 while formulation 2F with sorbital provided a much greater M-factor of 3.68.

Example 3

Optimization of Solvent Level in a Low Alcohol Mouth Rinse

To optimize solvent (ethanol, sorbitol, propylene glycol) levels for low-alcohol essential oil mouth rinse formulations, a central composite design was used for these three factors. Fifteen formulations were prepared and tested using the single-species *S. mutans* model described in Example 2, and log RLU was monitored to evaluate bioactivity. Sterile water was used as the negative control.

The fifteen formulations, as well as results of the *S. mutans* biofilm kill tests, are shown on Tables 3A and 3B. Final formulations were adjusted to pH 4.2 with 0.1M NaOH or 0.1M HCl if necessary. A typical M-factor for a commercially available alcohol containing essential oil mouth rinse is about 2.1 (log RLU of 5.8) in this model.

TABLE 3A

| Ingredients | 3A (% w/w) | 3B (% w/w) | 3C (% w/w) | 3D (% w/w) | 3E (% w/w) | 3F (% w/w) | 3G (% w/w) | 3H (% w/w) |
|---|---|---|---|---|---|---|---|---|
| Propylene glycol | 2.82 | 2.82 | 5.50 | 5.50 | 5.50 | 8.17 | 8.17 | 5.50 |
| Cremophor (PEG Castor Oil) | 0.1 | 0.1 | 0.1 | 0.1 | 0.1 | 0.1 | 0.1 | 0.1 |
| Ethanol | 2.02 | 7.97 | 10.00 | 5.00 | 5.00 | 2.03 | 2.02 | 5.00 |
| Benzoic Acid | 0.08 | 0.08 | 0.08 | 0.0 | 0.08 | 0.08 | 0.08 | 0.08 |
| Menthol | 0.042 | 0.042 | 0.042 | 0.042 | 0.042 | 0.042 | 0.042 | 0.042 |
| Methyl salicylate | 0.060 | 0.060 | 0.060 | 0.060 | 0.060 | 0.060 | 0.060 | 0.060 |
| Thymol | 0.064 | 0.064 | 0.064 | 0.064 | 0.064 | 0.064 | 0.064 | 0.064 |
| Eucalyptol | 0.092 | 0.092 | 0.092 | 0.092 | 0.092 | 0.092 | 0.092 | 0.092 |
| Sodium Lauryl Sulfate | 0.30 | 0.30 | 0.30 | 0.30 | 0.30 | 0.30 | 0.30 | 0.30 |
| Sorbitol (70% solution) | 15.94 | 4.05 | 10.00 | 10.00 | — | 4.05 | 15.94 | 20.00 |
| Sodium Benzoate | 0.07 | 0.07 | 0.07 | 0.07 | 0.07 | 0.07 | 0.07 | 0.07 |
| Flavor | 0.30 | 0.30 | 0.30 | 0.30 | 0.30 | 0.30 | 0.30 | 0.30 |
| Saccharin | 0.12 | 0.12 | 0.12 | 0.12 | 0.12 | 0.12 | 0.12 | 0.12 |

TABLE 3A-continued

| Ingredients | 3A (% w/w) | 3B (% w/w) | 3C (% w/w) | 3D (% w/w) | 3E (% w/w) | 3F (% w/w) | 3G (% w/w) | 3H (% w/w) |
|---|---|---|---|---|---|---|---|---|
| FD&C Green #3 | 0.0005 | 0.0005 | 0.0005 | 0.0005 | 0.0005 | 0.0005 | 0.0005 | 0.0005 |
| Purified Water USP | QS | QS | QS | QS | QS | QS | QS | QS |
| TOTAL | 100.0 | 100.0 | 100.0 | 100.0 | 100.0 | 100.0 | 100.0 | 100.0 |
| log RLU | 5.08 | 4.91 | 4.38 | 4.44 | 4.77 | 4.67 | 4.64 | 4.86 |
| M-factor | 2.82 | 2.99 | 3.52 | 3.46 | 3.13 | 3.23 | 3.26 | 3.04 |

TABLE 3B

| Ingredients | 3I (% w/w) | 3J (% w/w) | 3K (% w/w) | 3L (% w/w) | 3M (% w/w) | 3N (% w/w) | 3O (% w/w) | Negative Control (% w/w) |
|---|---|---|---|---|---|---|---|---|
| Propylene glycol | 2.82 | 8.18 | 8.18 | 5.50 | 2.82 | 1.00 | 10.00 | 100 |
| Cremophor (PEG Castor Oil) | 0.1 | 0.1 | 0.1 | 0.1 | 0.1 | 0.1 | 0.1 | — |
| Ethanol | 2.02 | 7.97 | 7.97 | — | 7.97 | 5.00 | 5.00 | — |
| Benzoic Acid | 0.08 | 0.08 | 0.08 | 0.08 | 0.08 | 0.08 | 0.08 | — |
| Menthol | 0.042 | 0.042 | 0.042 | 0.042 | 0.042 | 0.042 | 0.042 | — |
| Methyl salicylate | 0.060 | 0.060 | 0.060 | 0.060 | 0.060 | 0.060 | 0.060 | — |
| Thymol | 0.064 | 0.064 | 0.064 | 0.064 | 0.064 | 0.064 | 0.064 | — |
| Eucalyptol | 0.092 | 0.092 | 0.092 | 0.092 | 0.092 | 0.092 | 0.092 | — |
| Sodium Lauryl Sulfate | 0.30 | 0.30 | 0.30 | 0.30 | 0.30 | 0.30 | 0.30 | — |
| Sorbitol (70% solution) | 4.05 | 4.05 | 15.95 | 10.00 | 15.94 | 10.00 | 10.00 | — |
| Sodium Benzoate | 0.07 | 0.07 | 0.07 | 0.07 | 0.07 | 0.07 | 0.07 | — |
| Flavor | 0.30 | 0.30 | 0.30 | 0.30 | 0.30 | 0.30 | 0.30 | — |
| Saccharin | 0.12 | 0.12 | 0.12 | 0.12 | 0.12 | 0.12 | 0.12 | — |
| FD&C Green #3 | 0.0005 | 0.0005 | 0.0005 | 0.0005 | 0.0005 | 0.0005 | 0.0005 | — |
| Purified Water USP | QS | QS | QS | QS | QS | QS | QS | — |
| TOTAL | 100.0 | 100.0 | 100.0 | 100.0 | 100.0 | 100.0 | 100.0 | — |
| log RLU | 4.56 | 4.67 | 4.45 | 4.58 | 4.91 | 4.70 | 4.62 | 7.9 |
| M-factor | 3.34 | 3.29 | 3.45 | 3.32 | 2.99 | 3.2 | 3.28 | 0 |

As illustrated in Tables 3A and 3B, at a level of 0.3%, sodium lauryl sulfate and a total oil phase content of about 0.6% w/w, the propylene glycol (or polyol solvent) concentration is optimum between 4% and 10% w/w and sorbitol (or sugar alcohol solvent) is optimum between 6% and 14% w/w when added as a 70% sorbitol solution. Ethanol concentration did not have a large impact on efficacy in this system.

Example 4

Optimization of Solvent Levels in a Non-Alcohol Mouth Rinse with a Two-Factor Central Composite Design To optimize solvent (sorbitol, propylene glycol) levels for non-alcohol essential oil mouth rinse formulations, a central composite design was used for these two factors. Nine formulations were prepared and tested using the single-species S. mutans model described in Example 2, and log RLU was monitored to evaluate bioactivity. Sterile water was used as the negative control.

The nine formulations, as well as results of the S. mutans biofilm kill tests, are shown on Table 4. Final formulations were adjusted to pH 4.2 with 0.1M NaOH or 0.1M HCl if necessary. A typical M-factor for a commercially available alcohol containing essential oil mouth rinse is about 2.1 (log RLU of 5.8) in this model.

TABLE 4

| Ingredients | 4A (% w/w) | 4B (% w/w) | 4C (% w/w) | 4D (% w/w) | 4E (% w/w) | 4F (% w/w) | 4G (% w/w) | 4H (% w/w) | 4I (% w/w) | Negative Control (% w/w) |
|---|---|---|---|---|---|---|---|---|---|---|
| Propylene glycol | 7.20 | 7.20 | 12.50 | 12.50 | 17.80 | 5.00 | 12.50 | 17.80 | 20.00 | 100 |
| Menthol | 0.042 | 0.042 | 0.042 | 0.042 | 0.042 | 0.042 | 0.042 | 0.042 | 0.042 | |
| Methyl salicylate | 0.060 | 0.060 | 0.060 | 0.060 | 0.060 | 0.060 | 0.060 | 0.060 | 0.060 | |
| Thymol | 0.065 | 0.065 | 0.065 | 0.065 | 0.065 | 0.065 | 0.065 | 0.065 | 0.065 | |
| Eucalyptol | 0.093 | 0.093 | 0.093 | 0.093 | 0.093 | 0.093 | 0.093 | 0.093 | 0.093 | |
| Flavor | 0.10 | 0.10 | 0.10 | 0.10 | 0.10 | 0.10 | 0.10 | 0.10 | 0.10 | |
| Sorbitol (70% solution) | 3.66 | 21.34 | 25.00 | — | 21.34 | 12.50 | 12.50 | 3.66 | 12.50 | |
| Sodium Lauryl Sulfate | 0.35 | 0.35 | 0.35 | 0.35 | 0.35 | 0.35 | 0.35 | 0.35 | 0.35 | |
| Purified Water USP | QS | QS | QS | QS | QS | QS | QS | QS | QS | |
| Benzoic Acid | 0.086 | 0.086 | 0.086 | 0.086 | 0.086 | 0.086 | 0.086 | 0.086 | 0.086 | |
| Sodium Benzoate | 0.077 | 0.077 | 0.077 | 0.077 | 0.077 | 0.077 | 0.077 | 0.077 | 0.077 | |
| Saccharin | 0.06 | 0.06 | 0.06 | 0.06 | 0.06 | 0.06 | 0.06 | 0.06 | 0.06 | |
| Sucralose | 0.01 | 0.01 | 0.01 | 0.01 | 0.01 | 0.01 | 0.01 | 0.01 | 0.01 | |
| FD&C Green #3 | 0.0005 | 0.0005 | 0.0005 | 0.0005 | 0.0005 | 0.0005 | 0.0005 | 0.0005 | 0.0005 | |
| TOTAL | 100.0 | 100.0 | 100.0 | 100.0 | 100.0 | 100.0 | 100.0 | 100.0 | 100.0 | |
| log RLU | 5.96 | 5.44 | 5.57 | 5.69 | 5.77 | 5.27 | 5.38 | 5.8 | 5.87 | 7.94 |
| M-factor | 1.98 | 2.50 | 2.37 | 2.25 | 2.17 | 2.67 | 2.56 | 2.14 | 2.07 | 0 |

As illustrated in Table 4, at a level of 0.35% w/w sodium lauryl sulfate, and a total oil phase content of about 0.36% w/w, the propylene glycol (or polyol solvent) concentration is optimum between 5 and 13% w/w while sorbitol (or sugar alcohol solvent) is optimum between 10 and 25% w/w when added as a 70% sorbitol solution. Solvent optimums can vary depending on surfactant concentration and flavor choice.

Example 5

Evaluation of Other Glycol Solvents

Two formulations were prepared and tested using the single-species *S. mutans* model described in Example 2, with log RLU monitored to evaluate bioactivity. Sterile water was used as the negative control.

The purpose was to compare non-alcohol essential oil formulations containing propylene glycol to non-alcohol essential oil formulations containing other glycol solvents, such as 1,3-propanediol.

The formulations, as well as results of the *S. mutans* biofilm kill tests, are shown on Table 5. Final formulations were adjusted to pH 4.2 with 0.1M NaOH or 0.1M HCl if necessary. A typical M-factor for a commercially available alcohol containing essential oil mouth rinse is about 2.1 (log RLU of 5.8) in this model.

TABLE 5

| Ingredients | 5A (% w/w) | 5B (% w/w) | Negative Control (% w/w) |
|---|---|---|---|
| Purified Water USP | QS | QS | 100 |
| Sorbitol (70% solution) | 10.00 | 10.00 | — |
| 1,3-propanediol | 7.00 | — | — |
| Propylene glycol | — | 7.00 | — |
| Sodium lauryl sulfate | 0.30 | 0.30 | — |
| Sodium Saccharin | 0.12 | 0.12 | — |
| Flavor | 0.10 | 0.10 | — |
| Benzoic Acid | 0.10 | 0.10 | — |
| Sodium Benzoate | 0.05 | 0.05 | — |
| Eucalyptol | 0.093 | 0.093 | — |
| Thymol | 0.065 | 0.065 | — |
| Methyl Salicylate | 0.060 | 0.060 | — |
| Menthol | 0.042 | 0.042 | — |
| FD&C Green #3 | 0.0005 | 0.0005 | — |
| TOTAL | 100.00 | 100.00 | — |
| log RLU | 4.35 | 4.42 | 7.94 |
| M-factor | 3.59 | 3.52 | 0 |

The RLU values for ATP from oral biofilms treated with formulation 5A (1,3-propanediol as the polyol solvent) and formulation 5B (propylene glycol as the polyol solvent)\ are very comparable (M-factors equaling 3.59 and 3.52, respectively), indicating that propylene glycol can potentially be substituted with other polyol solvents (i.e., 1,3-propanediol) and still retain bioactivity. A typical M-factor for a commercially available alcohol containing essential oil mouth rinse is about 2.1 (log RLU of 5.8) in this model.

Example 6

Effect of Poloxamer

Four formulations were prepared and tested for mixed-species biofilm kill using the single species model discussed in Example 2. The negative control was sterile water.

The four formulations, as well as results of the single species biofilm kill tests, are shown on Table 6. Final formulations were adjusted to pH 4.2 with 0.1M NaOH or 0.1M HCl if necessary. A typical M-factor for a commercially available alcohol containing essential oil mouth rinse is about 2.1 (log RLU of 5.8) in this model.

TABLE 6

| | Formulations | | | | |
| --- | --- | --- | --- | --- | --- |
| Ingredients | 6A (% w/w) | 6B (% w/w) | 6C (% w/w) | 6D (% w/w) | Negative Control (% w/w) |
| Propylene glycol | 7.00 | 7.00 | 7.00 | 7.00 | 100 |
| Menthol | 0.042 | 0.042 | 0.042 | 0.042 | — |
| Methyl salicylate | 0.060 | 0.060 | 0.060 | 0.060 | — |
| Thymol | 0.065 | 0.065 | 0.065 | 0.065 | — |
| Eucalyptol | 0.093 | 0.093 | 0.093 | 0.093 | — |
| Flavor | 0.100 | 0.100 | 0.100 | 0.100 | — |
| Sorbitol | 10.00 | 10.00 | 10.00 | 10.00 | — |
| Sodium lauryl sulfate | 0.35 | 0.20 | 0.20 | 0.20 | — |
| Poloxamer 407 | 0.00 | 0.20 | 0.50 | 0.75 | — |
| Purified Water USP | QS | QS | QS | QS | — |
| Benzoic Acid | 0.086 | 0.086 | 0.086 | 0.086 | — |
| Sodium Benzoate | 0.077 | 0.077 | 0.077 | 0.077 | — |
| Saccharin | 0.060 | 0.060 | 0.060 | 0.060 | — |
| Sucralose | 0.01 | 0.01 | 0.01 | 0.01 | — |
| FD&C Green #3 | 0.0005 | 0.0005 | 0.0005 | 0.0005 | — |
| TOTAL | 100.0 | 100.0 | 100.0 | 100.0 | — |
| log RLU | 6.25 | 6.60 | 7.20 | 7.52 | 7.94 |
| M-factor | 1.69 | 1.34 | 0.74 | 0.42 | 0 |

The log RLU for water was 7.94. The table shows that as the amount of Poloxamer 407 added to the formulation was increased, the log RLUs (relative light units) increased. Increasing log RLUs indicates more viable bacteria remaining on the substrate. So, compositions free of Poloxamer are more effective on single species biofilm. The M-factors for all the formulations containing Poloxamer 407 (formulations 6B-6D) were less than 1.50.

Example 7

Evaluation of Glycerin as a Glycol Solvent

Six formulations were prepared and tested using the single-species *S. mutans* model described in Example 2, with log RLU monitored to evaluate bioactivity. Sterile water was used as the negative control.

The purpose was to compare non-alcohol essential oil formulations containing propylene glycol to non-alcohol essential oil formulations containing glycerin or glycerin/propylene glycol combinations.

The formulations, as well as results of the *S. mutans* biofilm kill tests, are shown on Table 7. Final formulations were adjusted to pH 4.2 with 0.1M NaOH or 0.1M HCl if necessary. A typical M-factor for a commercially available alcohol containing essential oil mouth rinse is about 2.1 (log RLU of 5.8) in this model.

TABLE 7

| | Formulations | | | | | | |
| --- | --- | --- | --- | --- | --- | --- | --- |
| Ingredients | 7A (% w/w) | 7B (% w/w) | 7C (% w/w) | 7D (% w/w) | 7E (% w/w) | 7F (% w/w) | Negative Control (% w/w) |
| Propylene glycol | 10.000 | 5.000 | — | 5.000 | — | — | — |
| Glycerin | — | 5.000 | 10.000 | 10.000 | 20.000 | 5.000 | — |
| Sorbitol | — | — | — | — | — | 10.000 | — |
| Benzoic Acid | 0.100 | 0.100 | 0.100 | 0.100 | 0.100 | 0.100 | — |
| Menthol | 0.042 | 0.042 | 0.042 | 0.042 | 0.042 | 0.042 | — |
| Methyl salicylate | 0.060 | 0.060 | 0.060 | 0.060 | 0.060 | 0.060 | — |
| Thymol | 0.064 | 0.064 | 0.064 | 0.064 | 0.064 | 0.064 | — |
| Eucalyptol | 0.092 | 0.092 | 0.092 | 0.092 | 0.092 | 0.092 | — |
| Sodium lauryl sulfate | 0.350 | 0.350 | 0.350 | 0.350 | 0.350 | 0.350 | — |
| Sodium Benzoate | 0.080 | 0.080 | 0.080 | 0.080 | 0.080 | 0.080 | — |
| Purified Water USP | QS | QS | QS | QS | QS | QS | 100 |
| TOTAL | 100 | 100 | 100 | 100 | 100 | 100 | — |
| log RLU | 6.20 | 6.65 | 6.30 | 6.32 | 6.46 | 6.12 | 7.9 |
| M-factor | 1.7 | 1.25 | 1.6 | 1.58 | 1.44 | 1.78 | 0 |

The log RLU values based on ATP from oral biofilms treated with both formulations are very comparable, indicating that propylene glycol can potentially be substituted with other glycol solvents and bioactivity will be maintained. The log RLU values based on ATP from oral biofilms treated with formulation 7A (propylene glycol) and formulation 7C (glycerin) are comparable (M-factors equaling 1.7 and 1.6, respectively), indicating that propylene glycol can potentially be substituted with other polyol solvents (i.e., glycerin) and still retain bioactivity.

Example 8

Combination of SLS with Other Surfactants

Three formulations were prepared and tested for mixed-species biofilm kill using a flow-through model, as shown in Example 1. Sterile water was used as the negative control.

The three formulations, as well as results of the mixed-species biofilm kill tests, are shown on Table 8. Final formulations were adjusted to pH 4.2 with 0.1M NaOH or 0.1M HCl if necessary. A typical M-factor for a commercially available alcohol containing essential oil mouth rinse is about 1.8 (log RLU of 5.7) in this model.

TABLE 8

| | Formulations | | | |
| --- | --- | --- | --- | --- |
| Ingredients | 8A (% w/w) | 8B (% w/w) | 8C (% w/w) | Negative Control (% w/w) |
| Propylene glycol | 7.00 | 0.00 | 0.00 | — |
| Glycerin | 0.00 | 10.00 | 10.00 | — |
| Menthol | 0.042 | 0.042 | 0.042 | — |
| Methyl salicylate | 0.060 | 0.060 | 0.060 | — |
| Thymol | 0.064 | 0.064 | 0.064 | — |
| Eucalyptol | 0.092 | 0.092 | 0.092 | — |
| Flavor | 0.100 | 0.100 | 0.100 | — |
| Sorbitol | 10.00 | 10.00 | 10.00 | — |
| Sodium lauryl sulfate | 0.35 | 0.15 | 0.00 | — |
| Sodium methyl cocoyl taurate | 0.00 | 0.15 | 0.30 | — |
| Purified Water USP | QS | QS | QS | 100 |
| Benzoic Acid | 0.086 | 0.086 | 0.086 | — |
| Sodium Benzoate | 0.077 | 0.077 | 0.077 | — |
| FD&C Green #3 | 0.0005 | 0.0005 | 0.0005 | — |
| TOTAL | 100.0 | 100.0 | 100.0 | — |
| log RLU | 5.47 | 5.18 | 6.29 | 7.5 |
| M-factor | 2.03 | 2.32 | 1.21 | 0 |

The log RLU values for ATP from oral biofilms treated with sodium lauryl sulfate and sodium lauryl sulfate/sodium methyl cocoyl taurate formulations are very comparable, indicating that the sodium lauryl sulfate level can be reduced when an additional surfactant (e.g, sodium methyl cocoyl taurate) is added to the formulation (as indicated by M-factors of 2.03 and 2.32, respectively) and bioactivity will be maintained. If no alkyl sulfate surfactant is present, a loss of bioactivity is observed (as indicated by the lower M-factor of 1.21).

What is claimed is:

1. A reduced-alcohol antimicrobial mouth rinse composition comprising:
   a. an oil phase comprising one or more antimicrobial essential oils;
   b. a solvent system comprising:
      i. at least one polyol solvent; and
      ii. at least one sugar alcohol solvent in an amount not exceeding 17% w/v of the composition; wherein said total amount of all polyol solvents and sugar alcohol solvents does not exceed 20% w/v of the composition;
   c. at least one alkyl sulfate surfactant;
   d. optionally, at least one other surfactant; and
   e. an aqueous phase comprising water
   wherein the mouth rinse composition is a microemulsion comprising micelles having an aggregate size less than about 200 nm and wherein the composition is free of bioavailability affecting compounds and further wherein the composition contains up to about 5% v/v of $C_2$ to $C_4$ monohydric alcohols.

2. A mouth rinse according to claim 1, wherein the antimicrobial essential oils are selected from the group consisting of menthol, eucalyptol, methyl salicylate, thymol and mixtures thereof.

3. A mouth rinse according to claim 2, wherein the antimicrobial essential oils are a mixture of menthol, eucalyptol, methyl salicylate and thymol.

4. A mouth rinse according to claim 1, wherein the polyol solvent is selected from the group consisting of polyhydric alkanes, polyhydric alkane esters, polyalkene glycols and mixtures thereof.

5. A mouth rinse according to claim 4, wherein the polyol is a polyhydric alkane.

6. A mouth rinse according to claim 5, wherein the polyhydric alkane is propylene glycol.

7. A mouth rinse according to claim 1, wherein the sugar alcohol solvent is selected from as the group consisting of xylitol, sorbitol, mannitol, maltitol, inositol, allitol, altritol, dulcitol, galactitol, glucitol, hexitol, iditol, pentitol, ribitol, erythritol and mixtures thereof.

8. A mouth rinse according to claim 7, wherein the sugar alcohol solvent is sorbitol.

9. A mouth rinse according to claim 1, wherein the polyol solvent and the sugar alcohol solvent are present at a ratio of from about 10:1 to about 1:10 by weight.

10. A mouth rinse according to claim 9, wherein the polyol solvent and the sugar alcohol solvent are present at a ratio of from about 5:1 to about 1:5 by weight.

11. A mouth rinse according to claim 1, wherein the alkyl sulfate surfactant is an alkyl sulfate surfactant having an even numbered $C_8$ to $C_{18}$ chain length.

12. A mouth rinse according to claim 11, wherein the alkyl sulfate surfactant is selected from the group consisting of sodium lauryl sulfate, hexadecyl sulfate and mixtures thereof.

13. A mouth rinse according to claim 1, wherein the ratio of the oil phase to solvent system to the alkyl sulfate surfactant in the composition is about 1:60:1.5 by weight.

14. A mouth rinse according to claim 13, wherein the ratio of the oil phase to the solvent system to the alkyl sulfate surfactant in the composition is about 1:200:1.5 by weight.

15. A mouthrinse according to claim 1, wherein the bioavailability affecting compounds are selected from the group consisting of polyethylene oxide/polypropylene oxide block copolymers such as poloxamers, cyclodextrins, polysorbates and mixtures.

16. A mouthrinse according to claim 1, wherein the composition is free of bioavailability affecting compounds.

17. A mouthrinse according to claim 1, wherein the composition is free of $C_2$-$C_4$ monohydric alcohols.

18. A mouthrinse according to claim 1, wherein the composition has an M-factor greater than about 0.5.

19. A mouthrinse according to claim 16, wherein the composition has an M-factor greater than about 1.0.

20. A reduced-alcohol antimicrobial mouth rinse composition comprising:

a. an oil phase comprising one or more antimicrobial essential oils;
b. a solvent system comprising:
   i. at least one polyol solvent; and
   ii. at least one sugar alcohol solvent in an amount not exceeding 17% w/v of the composition; said total amount of all polyol solvents and sugar alcohol solvents being present in an amount not exceeding 20% w/v of the composition;
c. at least one alkyl sulfate surfactant;
d. an aqueous phase comprising water
wherein the composition is free of bioavailability affecting compounds selected from the group consisting of polyethylene oxide/polypropylene oxide block copolymers and further wherein the composition contains up to 5% v/v of $C_2$ to $C_4$ monohydric alcohols.

* * * * *

UNITED STATES PATENT AND TRADEMARK OFFICE
CERTIFICATE OF CORRECTION

| | | |
|---|---|---|
| PATENT NO. | : 9,084,902 B2 | Page 1 of 1 |
| APPLICATION NO. | : 12/827927 | |
| DATED | : July 21, 2015 | |
| INVENTOR(S) | : Carolyn J. Mordas et al. | |

It is certified that error appears in the above-identified patent and that said Letters Patent is hereby corrected as shown below:

On The Title Page, Item (54) please delete the incorrect word "ALCHOHOL" in the title and replace with the word ALCOHOL.

Signed and Sealed this
Third Day of May, 2016

Michelle K. Lee
*Director of the United States Patent and Trademark Office*